(12) United States Patent
Chen et al.

(10) Patent No.: US 12,114,925 B2
(45) Date of Patent: Oct. 15, 2024

(54) ARTIFICIAL INTELLIGENCE EYE DISEASE SCREENING AND DIAGNOSTIC SYSTEM BASED ON OPHTHALMIC ROBOT

(71) Applicant: Ning Bo Eye Hospital, Zhejiang (CN)

(72) Inventors: Wei Chen, Zhejiang (CN); Zhongwen Li, Zhejiang (CN); Qinxiang Zheng, Zhejiang (CN)

(73) Assignee: Ning Bo Eye Hospital, Ningbo (CN)

( * ) Notice: Subject to any disclaimer, the term of this patent is extended or adjusted under 35 U.S.C. 154(b) by 557 days.

(21) Appl. No.: 17/463,289

(22) Filed: Aug. 31, 2021

(65) Prior Publication Data
US 2022/0079429 A1   Mar. 17, 2022

(30) Foreign Application Priority Data
Sep. 11, 2020 (CN) .......................... 202010954218.6

(51) Int. Cl.
| | |
|---|---|
| A61B 3/00 | (2006.01) |
| A61B 3/107 | (2006.01) |
| A61B 3/117 | (2006.01) |
| A61B 3/12 | (2006.01) |
| G06T 7/00 | (2017.01) |
| G16H 30/40 | (2018.01) |
| G16H 40/63 | (2018.01) |
| G16H 50/20 | (2018.01) |

(52) U.S. Cl.
CPC ............ *A61B 3/0016* (2013.01); *A61B 3/107* (2013.01); *A61B 3/117* (2013.01); *A61B 3/12* (2013.01); *G06T 7/0012* (2013.01); *G16H 30/40* (2018.01); *G16H 40/63* (2018.01); *G16H 50/20* (2018.01); *G06T 2207/20081* (2013.01); *G06T 2207/20084* (2013.01); *G06T 2207/30041* (2013.01); *G06T 2207/30096* (2013.01); *G06T 2207/30168* (2013.01)

(58) Field of Classification Search
CPC ....... A61B 3/0016; A61B 3/107; A61B 3/117; A61B 3/12; A61B 3/0025; A61B 3/0083; A61B 3/113; G06T 7/0012; G06T 2207/20081; G06T 2207/20084; G06T 2207/30041; G06T 2207/30096; G06T 2207/30168; G16H 30/40; G16H 40/63; G16H 50/20; G06N 3/045; G06N 3/08; G06V 40/19; G06V 40/168; G06V 40/193
USPC ........................................ 351/200, 205, 206
See application file for complete search history.

(56) References Cited

U.S. PATENT DOCUMENTS

2019/0274536 A1* 9/2019 Askarian .................. A61B 3/14

FOREIGN PATENT DOCUMENTS

WO   WO-2020112757 A1 *  6/2020  ........... A61B 3/0008

\* cited by examiner

*Primary Examiner* — Tuyen Tra

(57) ABSTRACT

An artificial intelligence eye disease screening and diagnostic system based on an ophthalmic robot, comprising a human eye positioning analysis module, an image information collection module, an AI picture quality monitoring module, an eye disease analysis and diagnosis module, a data storage management module, and an execution control module. The system can replace ophthalmologists to perform eye disease diagnosis tasks in regions lacking ophthalmologists, and assists the ophthalmologists in eye disease screening and diagnosis in large hospitals with a large number of patients, thus improving diagnosis efficiency.

13 Claims, 13 Drawing Sheets

ARTIFICIAL INTELLIGENCE EYE DISEASE SCREENING AND DIAGNOSTIC SYSTEM BASED ON OPHTHALMIC ROBOT

CROSS-REFERENCE TO RELATED APPLICATIONS

This application claims priority from Chinese patent application 202010954218.6 filed Sep. 11, 2020, the content of which are incorporated herein in the entirety by reference.

TECHNICAL FIELD

The present disclosure relates to the technical field of eye disease examination, and in particular to an artificial intelligence eye disease screening and diagnostic system based on an ophthalmic robot.

BACKGROUND

At present, the screening and diagnosis for eye diseases mainly rely on a manual examination by an ophthalmologist using a slit lamp or an ophthalmoscope to identify whether a patient has diseases of the ocular surface, the ocular anterior segment, or the ocular posterior segment. However, an artificial intelligence eye disease screening system researched and developed at present often either screens for fundus lesions alone or screens for certain ocular surface diseases alone, in other words, such system cannot intelligently screen for diseases of the whole eye from the ocular anterior segment to the ocular posterior segment. More importantly, the device equipped with the artificial intelligence system still requires professional personnel to operate.

Therefore, there is an urgent need to construct an artificial intelligence eye disease screening and diagnostic system comparable to the level of the ophthalmologist, the artificial intelligence eye disease screening and diagnostic system can be installed in an ophthalmic robot to make the ophthalmic robot be transformed into an intelligent ophthalmologist robot which can perform all-directional eye disease screening and diagnosis by replacing the professional ophthalmologist.

SUMMARY

To solve the technical problems, technical solutions adopted by the present disclosure is as follows:

in a first aspect: an artificial intelligence eye disease screening and diagnostic system based on an ophthalmic robot is provided, comprising:

a human eye positioning analysis module used for controlling the ophthalmic robot to position an eye of an examinee to determine eye positions of the examinee;

an execution control module used for executing a corresponding instruction to control the ophthalmic robot to move to the eye positions of the examinee;

an image information collection module used for acquiring ocular surface image data, ocular anterior segment image data, and fundus image data of the eye of the examinee;

an optometry information collection module used for synchronously acquiring diopter and corneal curvature of the eye of the examinee;

an AI picture quality monitoring module used for performing image quality judgement on the ocular surface image data, the ocular anterior segment image data, and the fundus image data of the eye of the examinee to determine the diagnostic image data of the examinee, wherein the ocular surface image data, the ocular anterior segment image data, and the fundus image data of the eye of the examinee are taken as the diagnostic image data if the ocular surface image data, the ocular anterior segment image data, and the fundus image data of the eye of the examinee are all qualified, and if at least one of the ocular surface image data, the ocular anterior segment image data, and the fundus image data of the eye of the examinee is unqualified, the image data of the unqualified part is reacquired for quality judgement until the ocular surface image data, the ocular anterior segment image data, and the fundus image data of the eye of the examinee are all qualified;

an eye disease analysis and diagnosis module used for analyzing eye disease symptoms according to the diagnostic image data, the diopter, and the corneal curvature of the eye of the examinee to determine the lesion types of the eye of the examinee;

and a data storage management module used for storing a diagnosis result generated by the eye disease analysis and diagnosis module and the image data acquired by the image information collection module.

In a second aspect, a method for performing eye disease screening and diagnosis using the system is provided, comprising:

S201, controlling the ophthalmic robot to position the eye of the examinee by the human eye positioning analysis module to determine the eye position of the examinee;

S202, executing a corresponding instruction by the execution control module to control the ophthalmic robot to move to the eye positions of the examinee;

S203, acquiring ocular surface image data, ocular anterior segment image data, and fundus image data of the eye of the examinee by the image information collection module, and synchronously acquiring diopter and corneal curvature of the eye of the examinee through the optometry information collection module;

S204, performing image quality judgement on the ocular surface image data, the ocular anterior segment image data, and the fundus image data of the eye of the examinee by the AI picture quality monitoring module, wherein the ocular surface image data, the ocular anterior segment image data, and the fundus image data of the eye of the examinee are taken as the diagnostic image data if the ocular surface image data, the ocular anterior segment image data, and the fundus image data of the eye of the examinee are all qualified, and if at least one of the ocular surface image data, the ocular anterior segment image data, and the fundus image data of the eye of the examinee is unqualified, the image data of the unqualified part is reacquired for quality judgement until the ocular surface image data, the ocular anterior segment image data, and the fundus image data of the eye of the examinee are all qualified;

S205, analyzing eye disease symptoms by the eye disease analysis and diagnosis module according to the diagnostic image data, the diopter, and the corneal curvature of the eye of the examinee to determine the lesion types of the eye of the examinee, and giving corresponding guidance and referral opinions by the ophthalmic robot;

and S206, storing a diagnosis result generated by the eye disease analysis and diagnosis module and the image data collected by the image information collection module by the data storage management module.

In an alternate way of the second aspect, analyzing the eye disease symptoms by the eye disease analysis and diagnosis module according to the diagnostic image data, the diopter, and the corneal curvature of the eye of the examinee to determine the lesion types of the eye of the examinee comprises: based on an ocular diagnosis algorithm model, analyzing the eye disease symptoms according to the diagnostic image data, the diopter, and the corneal curvature of the eye of the examinee to determine the lesion type of the eye of the examinee;

a construction method of the eye disease diagnosis algorithm model comprises:

S301, acquiring a training sample set consisting of the diagnostic image data, the diopter, and the corneal curvature of multiple examinees, and diagnosis results of multiple examinees, wherein the diagnosis results of the multiple examinees are obtained by ophthalmologists performing eye disease diagnosis according to the ocular surface image data, the ocular anterior segment image data, and the fundus image data of the multiple examinees;

Wherein the diagnosis result comprises, but is not limited to, the following eye diseases: eyelid diseases, ocular surface tumors, ptosis, refractive error, keratoconus, blepharitis, pterygium, conjunctivitis, keratitis, keratoconjunctivitis, anterior uveitis, hyphema, cataracts of different degrees, vitreous lesions, glaucomatous optic neuropathy, diabetic retinopathy, age-related macular degeneration, retinal vein occlusion, retinal artery occlusion, polypoidal choroidal vasculopathy, retinal detachment, macular hole, epiretinal membranes, macular edema, central serous chorioretinopathy, central exudative chorioretinopathy, retinal hemorrhage, retinal exudation, drusen, and the like;

and S302, based on the training sample set, training a preset convolutional neural network DenseNet121 using a deep learning algorithm to obtain the eye disease diagnosis algorithm model.

Based on hundreds of thousands of diagnosis results marked by the ophthalmologists, a deep learning algorithm is used for model training, verification, and testing to acquire the eye disease diagnosis algorithm model; accurate eye disease analysis and comparison are provided by the eye disease diagnosis algorithm model, and therefore the accuracy rate of eye disease screening and diagnosis for the examinee is improved, and the accuracy of the system is improved.

In an alternate way of the second aspect, the eye disease types comprise but are not limited to: refractive error, eyelid diseases such as hordeolum, conjunctival diseases such as conjunctivitis, corneal diseases such as keratitis, anterior chamber lesions such as anterior uveitis, cataract, vitreous lesions such as vitreous opacity, glaucoma, and fundus diseases such as diabetic retinopathy.

In an alternate way of the second aspect, a network structure of the eye disease diagnosis algorithm model is that:

the DenseNet121 serves as a splice for each layer, the input to each layer of the network comprises the outputs of all previous layers of the network, and the input to the L-th layer is equal to Kx+K0, where K is a growth rate, representing the number of channels for each layer. The DenseNet121 improves the transmission efficiency of information and gradient in the network, each layer can directly obtain the gradient from a loss function and directly obtain an input signal, and thus a deeper network can be trained; the network structure also has a regularization effect, other networks are dedicated to improving the network performance from depth and width, and the DenseNet121 is directed to improving the network performance from a feature reuse perspective.

The DenseNet121 has the following characteristics: the vanishing gradient is alleviated, the transfer of features is enhanced, the features are utilized more effectively, and the number of parameters is reduced to a certain extent; and on the premise of ensuring the maximum information transmission between the layers in the network, all the layers are directly connected.

In an alternate way of the second aspect, the training sample set further comprises at least one increment sample, the diagnostic image data of at least one examinee in the at least one increment sample is obtained by performing at least one of shading adjustment, rotation, and mirror inversion on the diagnostic image data of at least one examinee of the multiple examinees. The training sample set is expanded by the increment sample, thereby improving the accuracy of eye disease symptom analysis by the obtained eye disease diagnosis algorithm model.

In another alternate way of the second aspect, performing quality judgment on the ocular surface image data, the ocular anterior segment image data, and the fundus image data of the eye of the examinee by the AI picture quality monitoring module comprises: performing quality judgment on the ocular surface image data, the ocular anterior segment image data, and the fundus image data of the eye of the examinee based on an image quality judgment model to determine whether the ocular surface image data, the ocular anterior segment image data, and the fundus image data of the eye of the examinee are qualified; the image quality judgment model is a neural network model of DenseNet121 type.

In a third aspect, the artificial intelligence eye disease screening and diagnostic system is installed on an ophthalmic robot, and the ophthalmic robot is specifically a tabletop ophthalmic robot.

The present disclosure has the beneficial effects that:
(1) according to the artificial intelligence eye disease screening and diagnostic system based on the ophthalmic robot, an artificial intelligence eye disease screening and diagnostic system comparable to an ophthalmologist is constructed by utilizing a deep learning algorithm DenseNet121, and the artificial intelligence eye disease screening and diagnostic system is installed in the ophthalmic robot, and thus the ophthalmic robot can perform eye disease diagnosis tasks in regions lacking ophthalmologists replacing the ophthalmologists, and can automatically focus to respectively shoot the ocular surface, the ocular anterior segment and the fundus of the examinee and simultaneously perform automatic optometry and corneal curvature detection without being operated by professional personnel, thereby finding eye diseases in an early stage and giving timely guidance and referral; the ophthalmic robot can also assist in triage guidance and management in large hospitals with large number of patients, thus improving the disease diagnosis and treatment quality, and can assist non-ophthalmologists in diagnosis and treatment of the eye diseases in primary hospitals or general hospitals, thus reducing missed diagnosis and misdiagnosis rates.

(2) According to the artificial intelligence eye disease screening and diagnostic system based on the ophthalmic robot, the quality of the ocular surface image data, the ocular anterior segment image data and the fundus image data of the examinee is judged by the AI image quality monitoring system, thereby ensuring the quality of the diagnostic image data, and further guaranteeing the diagnosis and judgment accuracy of the artificial intelligence eye disease screening and diagnostic system.

(3) The ophthalmic robot designed by the present disclosure can efficiently collect and acquire information of the ocular surface, the ocular anterior segment and the fundus of the examinee and simultaneously perform automatic optometry and corneal curvature detection, thereby providing relatively accurate analysis information data for the diagnostic system, and improving the accuracy rate of eye disease screening and diagnosis for the examinee to further improve the accuracy of the system.

In which, 101—human eye positioning analysis module, 102—execution control module, 103—image information collection module, 104—optometry information collection module, 105—AI picture quality monitoring module, 106—eye disease analysis and diagnosis module, 107—data storage management module;

1—tabletop ophthalmic robot a, 11—robot main body, 12—robot base, 13—movable seat, 14—face support, 15—camera unit, 16—first display screen;

2—tabletop ophthalmic robot b, 21—main body lower portion, 22—main body upper portion, 23—second display screen, 24—face groove, 25—third motor sliding block, 26—cheekbone airbag supporting columns, 27—thermal camera, 28—imaging camera, 29—LED light bead;

3—chin rest, 31—hollow air plate, 32—airbag column, 33—pressure sensing wafer;

4—human eye information collection assembly, 41—camera assembly, 42—transmission rack, 42*a*—longitudinal bracket, 42*b*—transverse bracket, 43—first motor sliding block, 44—second motor sliding block;

5—transmission member, 52—rod main body, 52—toothed wheel, 521—branch tooth, 522—spur gear, 523—worm wheel, 53—worm, 54—transmission type toothed ring, 541—tooth socket, 55—driving motor set, 551—first rotating motor disc, 552—second rotating motor disc.

DETAILED DESCRIPTION OF THE EMBODIMENTS

Figure 1:
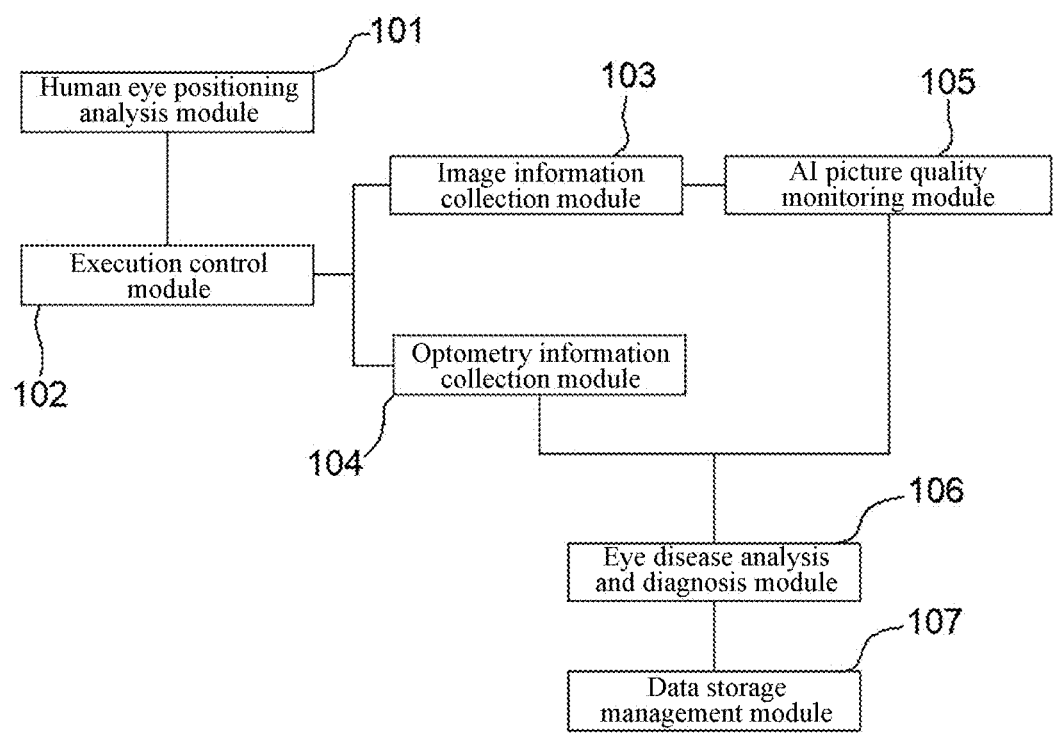
FIG. 1 is a system block diagram of an artificial intelligence eye disease screening and diagnostic system of the present disclosure.

Construction of Artificial Intelligence Eye Disease Screening and Diagnostic System As shown in FIG. 1, an artificial intelligence eye disease screening and diagnostic system based on an ophthalmic robot comprises: a human eye positioning analysis module 101 used for controlling the ophthalmic robot to position an eye of an examinee to determine an eye position of the examinee, wherein the human eye positioning analysis module 101 analyzes the eye position of the examinee according to a human eye positioning identification step of a camera assembly 41;

an execution module 102 used for executing a corresponding instruction to control the ophthalmic robot to move to the eye position of the examinee, wherein the execution control module 102 is used for achieving displaying of an analysis and diagnosis result through a second display screen 23, notification of a related operation instruction through the second display screen 23 or by voice, or driving of a human eye information collection assembly 4 according to an instruction, and the human eye information collection assembly 4 and other related components are instructed by the execution control module 102 to move to the eye position of the examinee;

an image information collection module 103 used for acquiring ocular surface image data, ocular anterior segment image data, and fundus image data of the eye of the examinee;

and an optometry information collection module 104 for synchronously acquiring diopter and corneal curvature of the eye of the examinee, wherein the image information collection module 103, the optometry information collection module 104 and the camera assembly 41 are used for acquiring the ocular surface image data, the ocular anterior segment image data and the fundus image data of the eye of the examinee and acquiring the diopter and the corneal curvature for the analysis and diagnosis of an eye disease analysis and diagnosis module 106;

an AI picture quality monitoring module 105 used for performing quality judgement on the ocular surface image data, the ocular anterior segment image data and the fundus image data of the eye of the examinee to determine diagnostic image data of the examinee; wherein the ocular surface image data, the ocular anterior segment image data and the fundus image data of the eye of the examinee are taken as the diagnostic image data if the ocular surface image data, the ocular anterior segment image data and the fundus image data of the eye of the examinee are all qualified; if at least one image data of the ocular surface image data, the ocular anterior segment image data and the fundus image data of the eye of the examinee is unqualified, the image data of the unqualified part is reacquired for quality judgement until the ocular surface image data, the ocular anterior segment image data and the fundus image data of the eye of the examinee are all qualified; performing quality judgment on the ocular surface image data, the ocular anterior segment image data and the fundus image data of the eye of the examinee by the AI picture quality monitoring module 105 comprises: performing quality judgment on the ocular surface image data, the ocular anterior segment image data and the fundus image data of the eye of the examinee based on an image quality judgment model to determine whether the ocular surface image data, the ocular anterior segment image data and the fundus image data of the eye of the examinee are qualified. The image quality judgment model is a neural network model of DenseNet121 type, and the image quality judgement model is constructed adopting a construction method same as that of an eye disease diagnosis algorithm model;

the eye disease analysis and diagnosis module 106 used for analyzing eye disease symptoms according to the diagnostic image data, the diopter, and the corneal curvature of the eye of the examinee to determine lesion types of the eye of the examinee, wherein the eye disease analysis and diagnosis module 106, based on the eye disease diagnosis algorithm model, is used for analyzing the eye disease symptoms according to the diagnostic image data, the diopter, and the corneal curvature of the eye of the examinee to determine the lesion types of the eye of the examinee, and corresponding guidance and referral opinions are given by the ophthalmic robot;

a data storage management module 107 used for storing a diagnosis result generated by the eye disease analysis and diagnosis module 106 and image data collected by the image information collection module 103, wherein the data storage management module 107 is used for storing the diagnostic image data, the diopter, the corneal curvature of the eye of the examinee, and the diagnostic analysis result, and caching related data information of operation diagnosis of the artificial intelligence eye disease screening and diagnostic system;

the artificial intelligence eye disease screening and diagnostic system is installed on a tabletop ophthalmic robot, the obtained eye information image of the examinee is high in quality and accuracy, and accurate analysis of eye disease screening and diagnosis of the ophthalmic robot with the artificial intelligence eye disease screening and diagnostic system is facilitated. Through the structure design, hard light or weak light is avoided during collection of the eye information of the examinee, and thus the accuracy of the eye information image of the examinee is improved, and meanwhile, a shape of chin is formed through the cooperation of multiple groups of dense airbag columns to stabilize and support the chin of the examinee, and the airbag columns are continuously inflated to extend outward to play a role of raising the chin.

Figure 2:
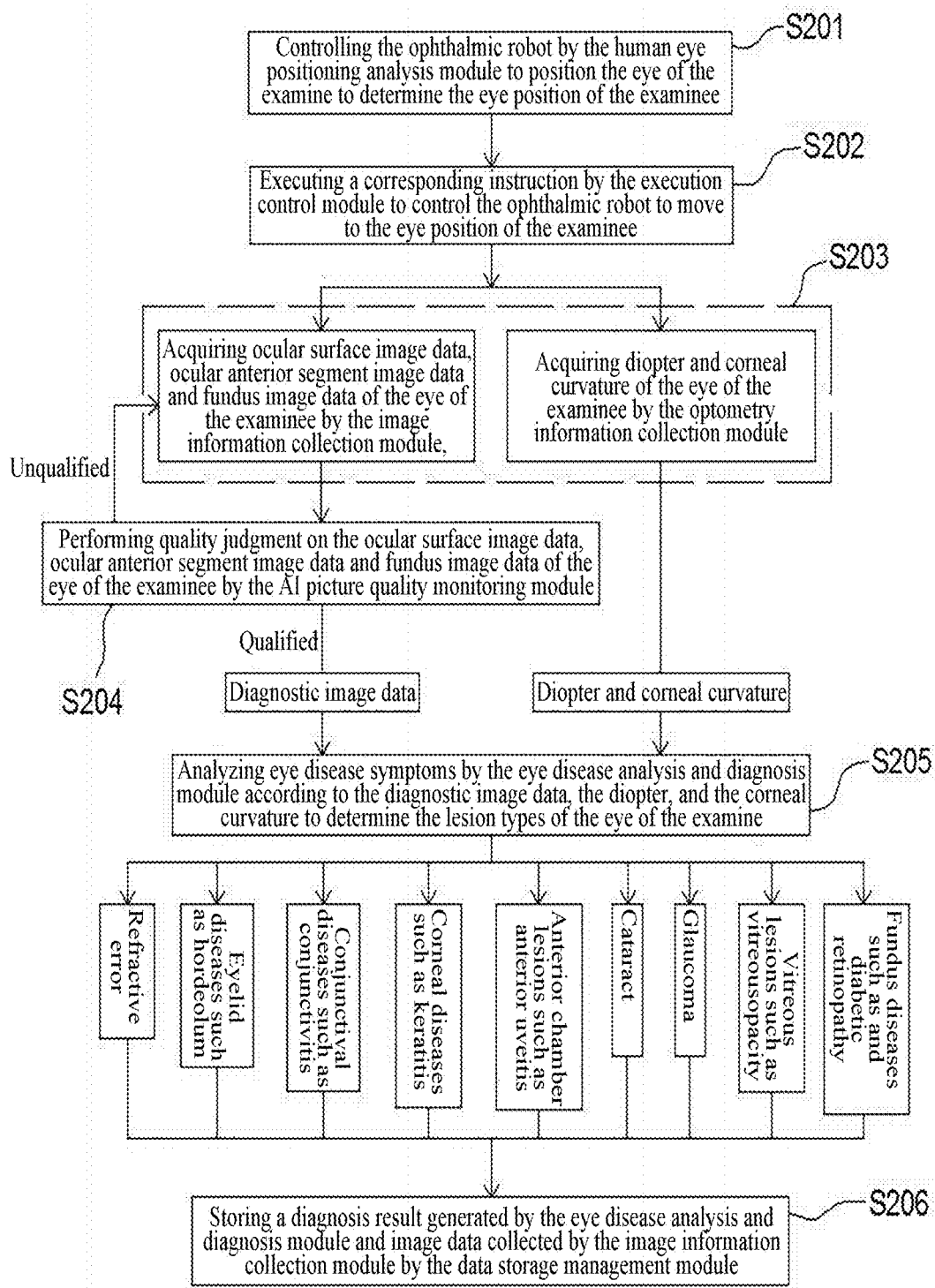
FIG. 2 is a flow block diagram of eye disease screening and diagnosis of an artificial intelligence eye disease screening and diagnostic system of the present disclosure.

As shown in FIG. 2, a method for performing eye disease screening and diagnosis using the artificial intelligence eye disease screening and diagnostic system comprises:

S201, controlling an ophthalmic robot to position an eye of an examinee by the human eye positioning analysis module 101 to determine an eye position of the examinee;

S202, executing a corresponding instruction by the execution control module 102 to control the ophthalmic robot to move to the eye position of the examinee;

S203, acquiring ocular surface image data, ocular anterior segment image data, and fundus image data of the eye of the examinee by the image information collection module 103, and synchronously acquiring diopter and corneal curvature of the eye of the examinee by the optometry information collection module 104;

S204, performing image quality judgement on the ocular surface image data, the ocular anterior segment image data, and the fundus image data of the eye of the examinee by the AI picture quality monitoring module 105, wherein the ocular surface image data, the ocular anterior segment image data, and the fundus image data of the eye of the examinee are taken as the diagnostic image data if the ocular surface image data, the ocular anterior segment image data, and the fundus image data of the eye of the examinee are all qualified, and if at least one of the ocular surface image data, the ocular anterior segment image data, and the fundus image data of the eye of the examinee is unqualified, the image data of the unqualified part is reacquired for quality judgement until the ocular surface image data, the ocular anterior segment image data, and the fundus image data of the eye of the examinee are all qualified;

S205, analyzing eye disease symptoms by the eye disease analysis and diagnosis module 106 according to the diagnostic image data, the diopter, and the corneal curvature of the eye of the examinee to determine the lesion types of the eye of the examinee, and giving corresponding guidance and referral opinions by the ophthalmic robot;

and S206, storing a diagnosis result generated by the eye disease analysis and diagnosis module 106 and the image data collected by the image information collection module 103 by the data storage management module 107;

the lesion types comprise, but are not limited to: refractive error, eyelid diseases such as hordeolum, conjunctival diseases such as conjunctivitis, corneal diseases such as keratitis, anterior chamber lesions such as anterior uveitis, cataract, vitreous lesions such as vitreous opacity, glaucoma, and fundus diseases such as diabetic retinopathy. For example, if refractive error is found, it is recommended to go to the ophthalmology department of a higher-level hospital for medical optometry; if glaucomatous optic neuropathy is found, it is recommended to go to the ophthalmology department of a higher-level hospital for glaucoma screening; if eyelid tumor is found, it is recommended to go to the ophthalmology department of a higher-level hospital to clarify the nature of the tumor.

Construction Method of Eye Disease Diagnosis Algorithm Model

Figure 3:
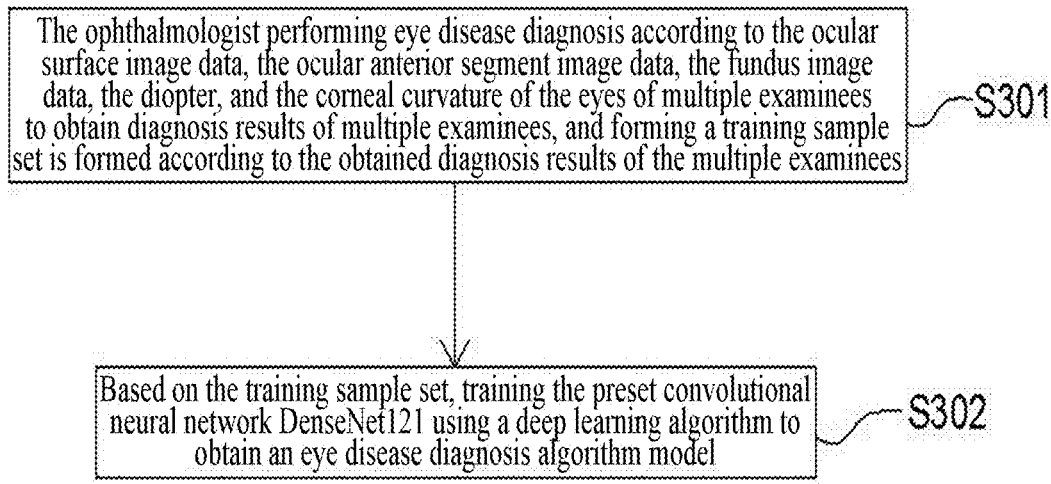
FIG. 3 is a flow diagram of a construction method of an eye disease diagnosis algorithm model of the present disclosure.

As shown in FIG. 3, a construction method of an eye disease diagnosis algorithm model comprises:

S301, acquiring a training sample set consisting of the diagnostic image data, the diopter and the corneal curvature of multiple examinees, and diagnosis results of the multiple examinees, wherein the diagnosis results of the multiple examinees are obtained by ophthalmologists performing eye disease diagnosis based on the ocular surface image data, the ocular anterior segment image data, the fundus image data, the diopter, and the corneal curvature of the multiple examinees in combination with clinical data of the examinees, including: basic information, disease history, specialist examination, examination results, special examination results, and the like;

the training sample set further comprises at least one increment sample, the diagnostic image data of at least one examinee in the at least one increment sample is obtained by performing at least one of shading adjustment, rotation and mirror inversion on the diagnostic image data of the at least one examinee in the multiple examinees, and the training sample set is expanded by the increment sample, and thus the accuracy of eye disease symptom analysis by the obtained eye disease diagnosis algorithm model is improved;

wherein the diagnosis results comprise but are not limited to the following eye diseases: eyelid diseases, ocular surface tumors, ptosis, refractive error, keratoconus, blepharitis, pterygium, conjunctivitis, keratitis, keratoconjunctivitis, anterior uveitis, hyphema, cataracts of different degrees, vitreous lesions, glaucomatous optic neuropathy, diabetic retinopathy, age-related macular degeneration, retinal vein occlusion, retinal artery occlusion, polypoidal choroidal vasculopathy, retinal detachment, macular hole, epiretinal membranes, macular edema, central serous chorioretinopathy, central exudative chorioretinopathy, retinal hemorrhage, retinal exudation, drusen, and the like;

and S302, based on the training sample set, training a preset convolutional neural network Kx(L−1)+k0 DenseNet121 using a deep learning algorithm to obtain the eye disease diagnosis algorithm model.

Based on hundreds of thousands of diagnosis results marked by ophthalmologists, the deep learning algorithm is used for model training, verification, and testing to obtain the eye disease diagnosis algorithm model; accurate eye disease analysis and comparison are provided by the eye disease diagnosis algorithm model, and therefore the accuracy rate of eye disease screening and diagnosis for the examinee is improved, and the accuracy of the system is improved.

Figure 4:
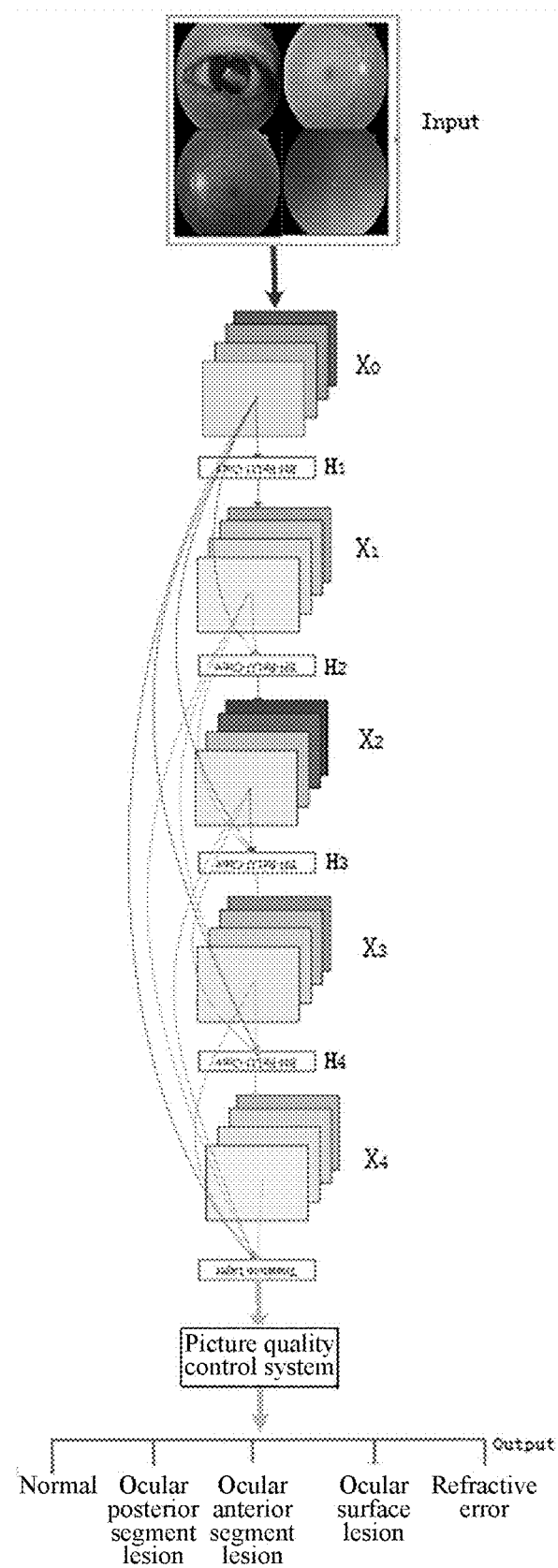
FIG. 4 is a schematic diagram of a network structure of an eye disease analysis and diagnosis module of the present disclosure.

A specific network structure of the eye disease diagnosis algorithm model is as shown in FIG. 4, DenseNet121 serves as a splice for each layer, the input to each layer of network comprises the outputs of all previous layers of network, and the input to the L-th layer is equal to K× (L−1)+k0, where K is a growth rate, representing the number of channels for each layer. For example, the number of channels of the network in FIG. 4 is 4, in the traditional convolutional neural network, there may be L connections if L layers are provided, however, in the DenseNet121, there may be L(L+1)/2 connections, that is, the input side to each layer is from the outputs of all previous layers, in FIG. 4, $X_0$ is input, the input to $H_1$ is $X_0$ (input), the input to $H_2$ is $X_0$ and $X_1$ ($H_1$ is output of $H_1$), and so forth;

the DenseNet121 has the following characteristics: the vanishing gradient is alleviated, the transfer of features is enhanced, the features are utilized more effectively, and the number of parameters is reduced to a certain extent; and on the premise of ensuring the maximum information transmission between the layers in the network, all the layers are directly connected.

A method for training the preset convolutional neural network DenseNet121 comprises:

step one, experimental algorithm setting:

using a SGD as an optimization algorithm, setting an initial learning rate (lr) corresponding to the algorithm as 0.001, momentum as 0.9, weight decay as $5\times10^{-5}$, epoch as 80, and batch size as 64; using a learning rate decay strategy in the training process: every 20 epochs, the learning rate decays to one tenth of the original, representing as:

Lr=lr*(0.1**(epoch//20)), that is, the formula is as follows:

$$Lr = lr \times (0.1^{(k//20)})$$

wherein, // takes the integer division operator, i.e., works out the integer part of the quotient (excluding the remainder), and k is the epoch;

a loss function used in experiment is a cross entropy loss:

$$Loss = -\sum_{i}^{n} p_i \log y_i$$

wherein, $P_i$ and $y_i$ respectively denote the prediction probability that a classification model predicts that the image is the i-th class and the real label of the image, and n is the total number of classes of classification;

step two, experimental environment:

in the experiment, constructing a network model of the experiment using Pytorch deep learning framework, and training simultaneously on four NVIDIA TITAN RTX GPUs with video memory of 24G;

step three, data preprocessing:

scaling the picture size of the data set to 224*224 in a unified manner to meet an input requirement of the network model, and meanwhile, for enhancing generalization ability of the model, randomly rotating the picture by 90 degrees, and flipping in a horizontal direction or a vertical direction, with a random probability of 0.5;

and step four, data set division:

randomly dividing the original data set into three parts: a training set, a verification set, and a testing part, accounting for 70%, 15, 15% respectively.

Construction of Ophthalmic Robot

In an embodiment of the present disclosure, alternately, an ophthalmic robot employs a tabletop ophthalmic robot a 1.

Figure 6:
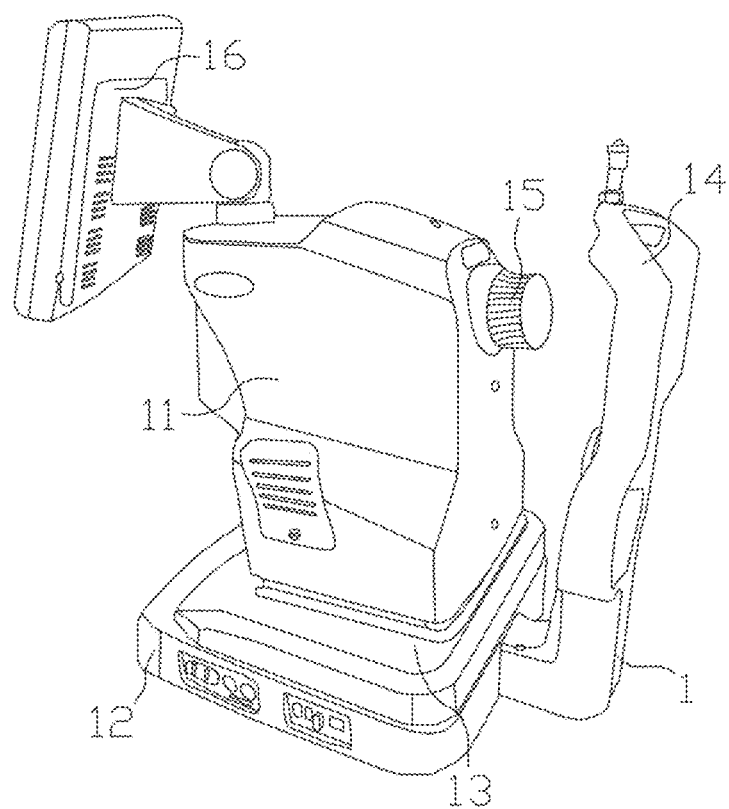
FIG. 6 is a schematic diagram of an entire structure of a tabletop ophthalmic robot a of the present disclosure.

As shown in FIG. 6, an artificial intelligence eye disease screening and diagnostic system is installed on a controller in a robot main body 11 of the tabletop ophthalmic robot a 1, the tabletop ophthalmic robot a 1 comprises: the robot main body 11 for information processing; a robot base 12 used for energy supply and support of each component; a movable seat 13 used for moving the robot main body 11; a face support 14 used for supporting the face and positioning a chin; and a first display screen 16 used for observing and displaying eye information of an examinee; the robot main body 11 is in sliding connection with the robot base 12 through a sliding chute and a sliding block by the movable seat 13, a side face upper portion, corresponding to the position of the face support 14, of the robot main body 11 is provided with a camera unit 15 used for obtaining the eye information of the examinee, and the first display screen 16 is connected to the front end of an upper surface of the robot main body 11 through a movable rotating shaft.

In an embodiment, alternately, the ophthalmic robot employs a tabletop ophthalmic robot b 2.

Figure 7:
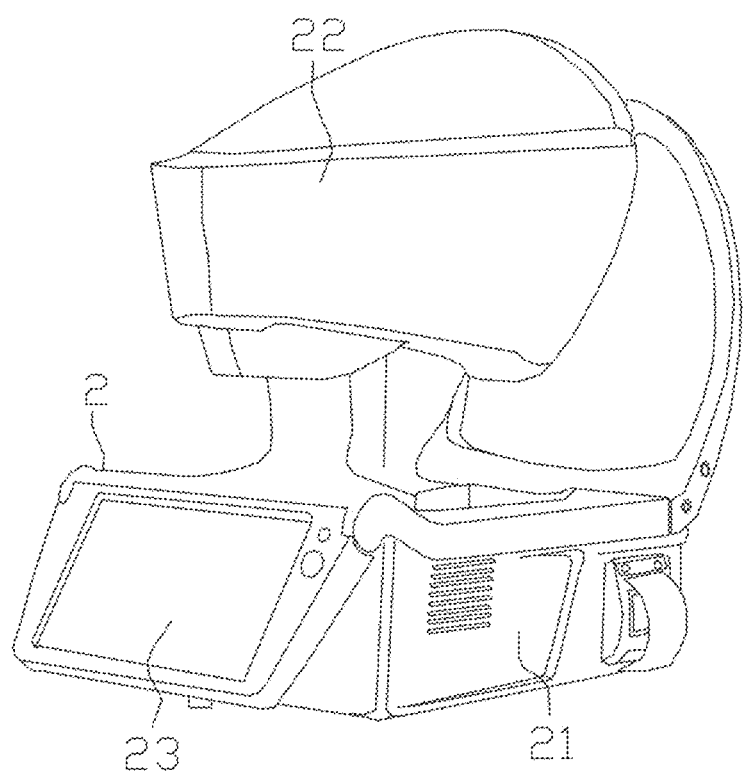
FIG. 7 is a schematic diagram of an entire structure of a tabletop ophthalmic robot b of the present disclosure.
Figure 8:
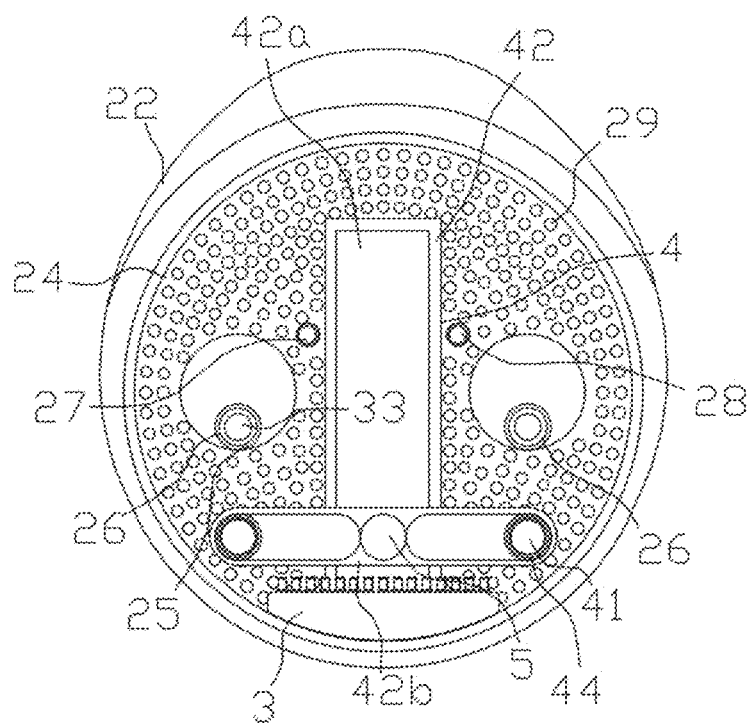
FIG. 8 is a front view of a face groove structure of a tabletop ophthalmic robot b of the present disclosure.
Figure 9:
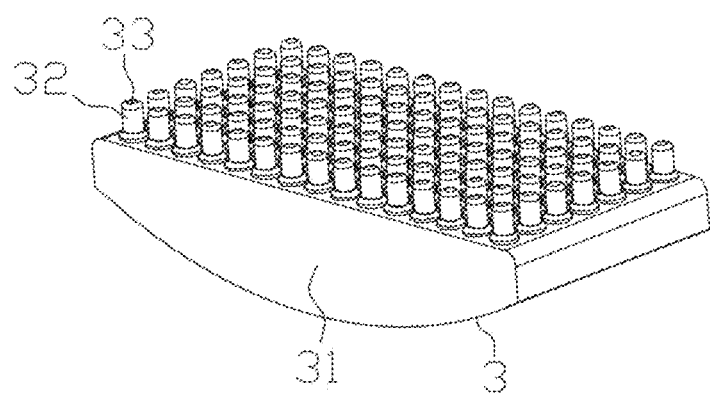
FIG. 9 is schematic diagram of a chin rest structure of a tabletop ophthalmic robot b of the present disclosure.
Figure 10:
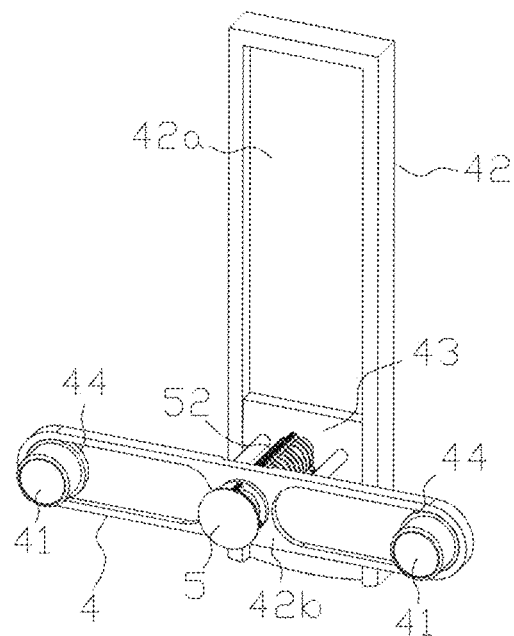
FIG. 10 is a schematic diagram of a front view of a human eye information collection assembly structure of a tabletop ophthalmic robot b of the present disclosure.
Figure 11:
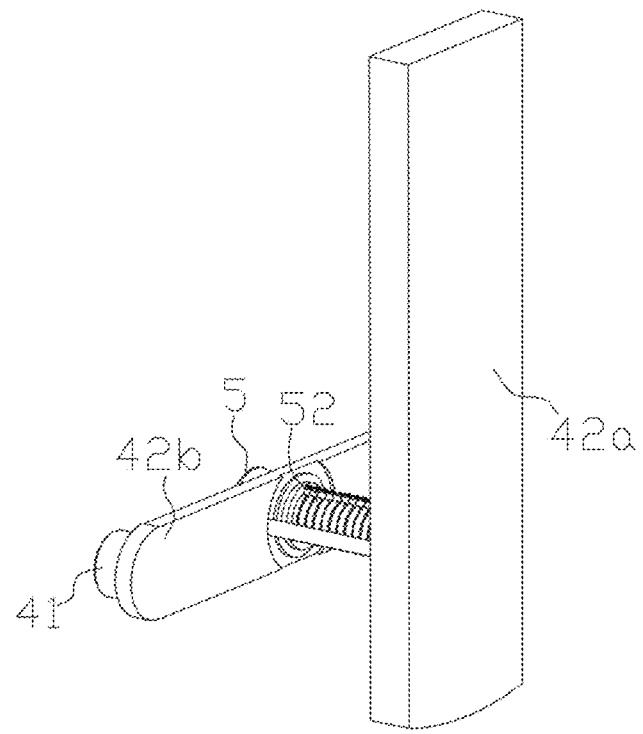
FIG. 11 is a schematic diagram of a rear view of a human eye information collection assembly structure of a tabletop ophthalmic robot b of the present disclosure.
Figure 12:
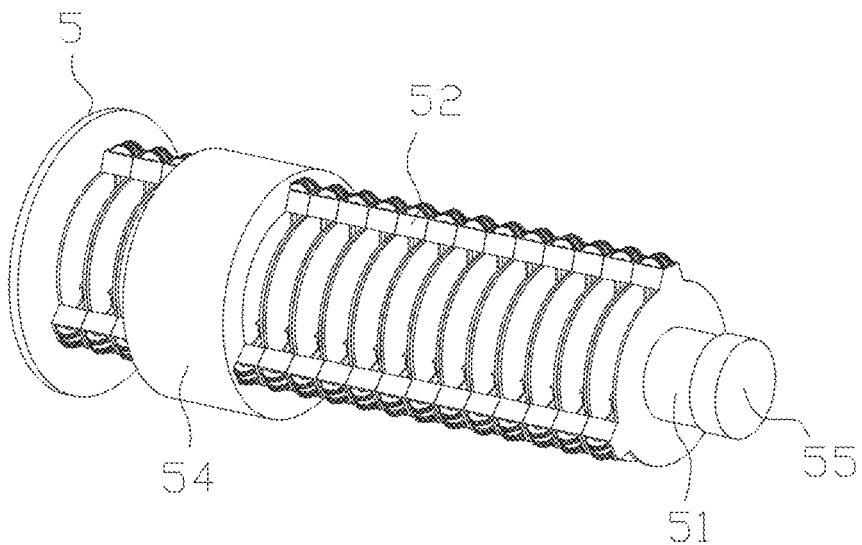
FIG. 12 is a structure diagram of a transmission member of a tabletop ophthalmic robot b of the present disclosure.
Figure 13:
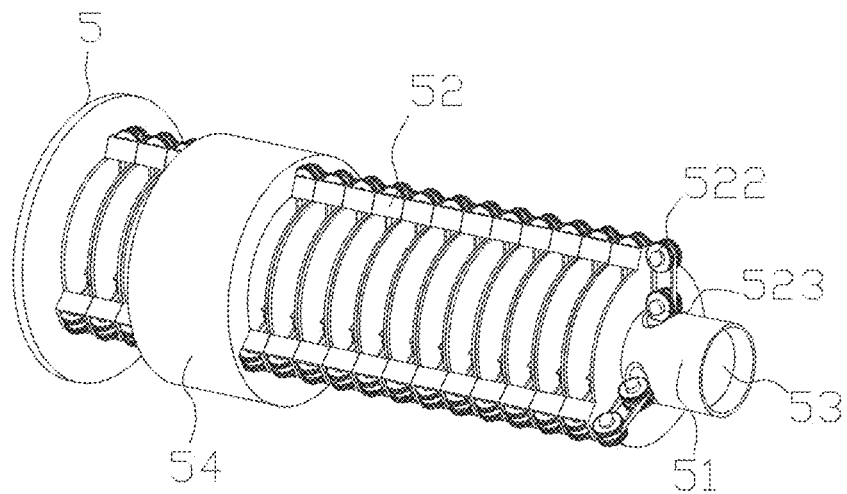
FIG. 13 is a schematic diagram of an internal structure of a transmission member of a tabletop ophthalmic robot b of the present disclosure.
Figure 14:
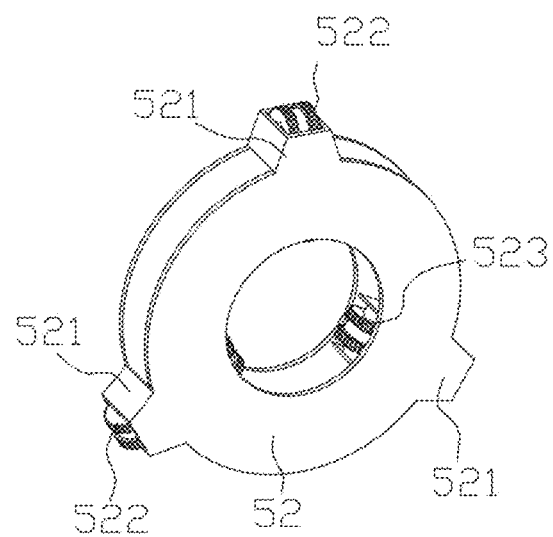
FIG. 14 is a structure diagram of a toothed wheel of a transmission member of a tabletop ophthalmic robot b of the present disclosure.
Figure 15:
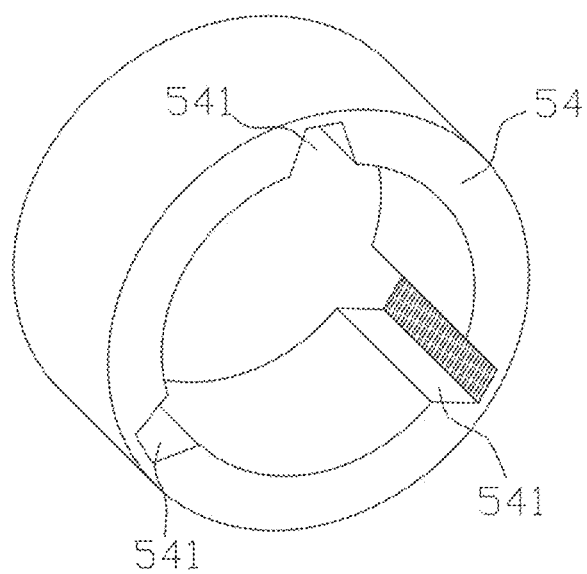
FIG. 15 is a structure diagram of a transmission type toothed ring of a transmission member of a tabletop ophthalmic robot b of the present disclosure.
Figure 16:
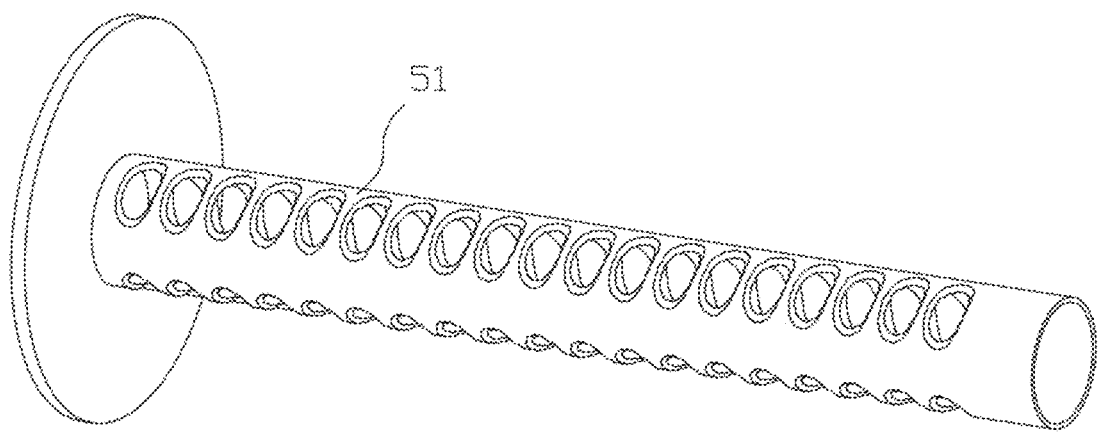
FIG. 16 is a structure diagram of a rod main body of a transmission member of a tabletop ophthalmic robot b of the present disclosure.
Figure 17:
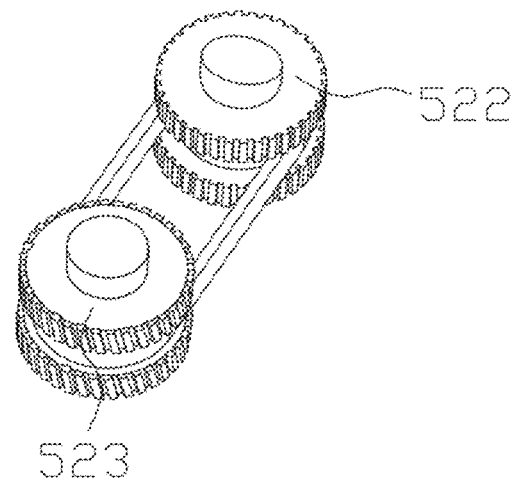
FIG. 17 is a schematic diagram of connection of a spur gear and a worm wheel of a transmission member of a tabletop ophthalmic robot b of the present disclosure.
Figure 18:
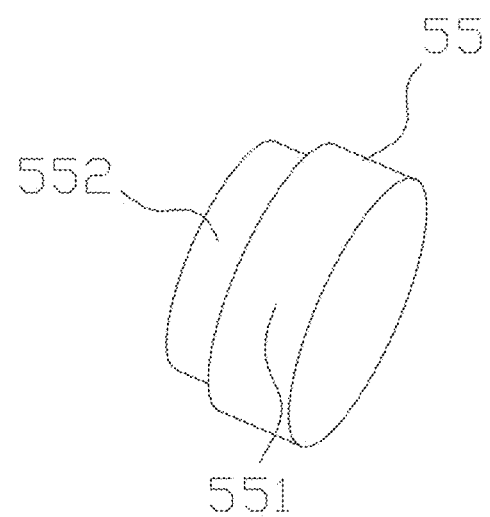
FIG. 18 is a structure diagram of a driving motor set of a transmission member of a tabletop ophthalmic robot b of the present disclosure.

As shown in FIG. 7, an artificial intelligence eye disease screening and diagnostic system is installed on a controller in a main body lower portion 21 of the tabletop ophthalmic robot b 2, the tabletop ophthalmic robot b 2 comprises: a combined special-shaped body consisting of a main body lower portion 21 used for energy supply and information processing and a main body upper portion 22 for loading components such as a human eye information collection assembly 4 and the like up and down, and the front end face of the main body lower portion 21 is provided with a second display screen 23 used for observing and displaying eye information of the examinee, as shown in FIG. 8, a face groove 24 is formed at the front side face of the main body upper portion 22, a chin rest 3 is arranged at the lower end in the face groove 24, the human eye information collection assembly 4 is arranged at an inner wall of the face groove 24, and cheekbone airbag supporting columns 26 which are connected through a third motor sliding block 25 are further arranged at the two ends of the inner wall of the face groove 24; an arc-shaped cotton cushion for avoiding head blow is further arranged at an upper top face in the face groove 24, a thermal camera 27 used for face thermal photographing of the face and an imaging camera 28 used for shooting and positioning the eye are further arranged at the middle portion of the inner wall of the face groove 24, and LED light beads 29 are uniformly and densely embedded on the inner wall of the face groove 24, as shown in FIG. 9, the chin rest 3 further comprises a hollow air plate 31 on which dense airbag columns 32 are equidistantly provided, and pressure sensing wafer s 33 are arranged at the front ends of the airbag columns 32 and the front ends of the cheekbone airbag supporting columns 26, as shown in FIG. 10 to FIG. 11, the human eye information collection assembly 4 comprises two symmetrically arranged camera assemblies 41, and a transmission rack 42; the transmission rack 42 comprises a longitudinal bracket 42a, and a transverse bracket 42b; the transmission rack 42 is connected to the lower bottom face of the face groove 24 through the bottom end of the longitudinal bracket 42a, the transverse bracket 42b is connected to a first motor sliding block 43 arranged on a motor sliding chute of the longitudinal bracket 42a through a transmission member 5, the first motor sliding blocks 43 at the two sides of the transmission member 5 is each provided with a telescopic rod to be in sliding connection with the transverse bracket 42b, and the camera assemblies 41 are connected to second motor sliding blocks 44 arranged on the motor sliding chutes at the two sides of the transverse bracket 42b, wherein, as shown in FIG. 12 to FIG. 18, the transmission member 5 comprises a rod main body 51, the rod main body 51 is equidistantly provided with multiple toothed wheels 52 which are fixedly connected to the rod main body 51, and two adjacent toothed wheels 52 are butted next to each other; each toothed wheel 52 is hollow inside, and is circumferentially provided with three branch teeth 321, the far end in each branch tooth 521 is provided with a spur gear 522 to be in rotatable connection with the inner wall of the branch teeth 521, the inner near end of each branch tooth 521 is provided with a worm wheel 523 to be in rotating connection with the inner wall of the toothed wheel 52, and the worm wheel 523 and the spur gear 522 are in transmission through a toothed belt; the rod main body 51 is hollow inside and is provided with a rotating worm to be in meshing transmission with each worm wheel 523, and a hole for abutting the worm 52 with the worm wheel 523 is formed in a position, corresponding to the worm wheel 523, of the rod main body 51; a transmission type toothed ring 54 is arranged at the outer circumference of each toothed wheel 52 in a sleeved manner, a tooth socket 541 of the transmission type toothed ring 54 is provided with a tooth surface in meshing transmission with the spur gear 522, and the transverse bracket 42b is arranged at the outer wall of the transmission type toothed ring 54 in a sleeved manner; a driving motor set 55 is arranged at the rear end of the rod main body 51 and is used for respectively driving the rod main body 51 to rotate and driving the worm 53 to rotate; the driving motor set 55 comprises a first rotating motor disc 551, and a second rotating motor disc 552; the second rotating motor disc 552 is fixed to the center of the first rotating motor disc 551, and is connected to the worm 53, and a circular area between the first rotating motor disc 551 and the second rotating motor disc 552 is connected to the rod main body 51;

an artificial intelligence eye disease screening and diagnostic system which is constructed using a deep convolutional neural network DenseNet121 training model and is used for picture quality control and eye disease screening and diagnosis is installed in the tabletop ophthalmic robot b 2. Wherein the thermal camera 27 employs a commercially available infrared thermal induction camera, and the thermal camera 27 is adjusted in shape to be adaptively installed at a designated position in the face groove 11; the imaging camera 28 employs a commercially available 50-million-pixel Zeiss lens, and the LED light beads 29 all employ commercially available brand LED light sources for shape adjustment and adaptation. The first motor sliding block, the second motor sliding block and the third motor sliding block all employ commercially available brand sliding rail motors for shape adjustment and adaptation, and the driving motor set 55 employs a small rotating motor for shape modification to meet the graphic structure.

Eye Positioning Method of Tabletop Ophthalmic Robot b 2

Figure 5:
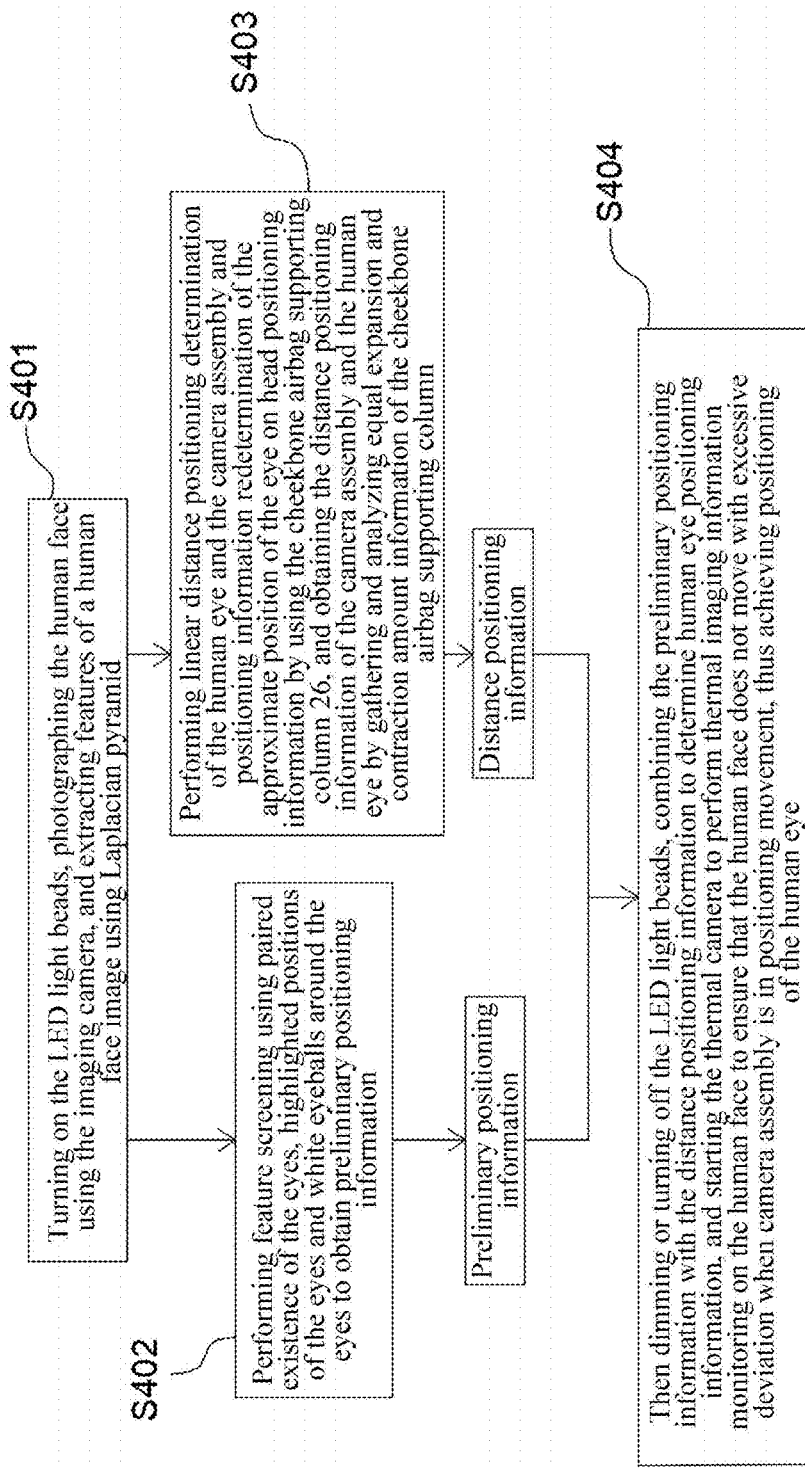
FIG. 5 is a schematic diagram of an eye positioning method of an ophthalmic robot of the present disclosure.

As shown in FIG. 5, the human eye positioning identification of the camera assembly comprises the following steps:

S401, turning on the LED light beads 29, photographing the human face using the imaging camera 28, and extracting features of a human face image using Laplacian pyramid;

S402, performing feature screening using paired existence of the eyes, highlighted positions of the eyes and white eyeballs around the eyes to obtain preliminary positioning information;

S403, performing linear distance positioning determination of the human eye and the camera assembly and positioning information redetermination of the approximate position of the eye on head positioning information by using the cheekbone airbag supporting column 26, and obtaining the distance positioning information of the camera assembly 41 and the human eye by gathering and analyzing equal expansion and contraction amount information of the cheekbone airbag supporting column 26;

and S404, then dimming or turning off the LED light beads 29, combining the preliminary positioning information in step S402 with the distance positioning information in step S403 to determine human eye positioning information, and starting the thermal camera 27 to perform thermal imaging information monitoring on the human face to ensure that the human face does not move with excessive deviation when camera assembly 41 is in positioning movement, thus achieving positioning of the human eye.

Tabletop Ophthalmic Robot b 2 and Diagnosis System Examination Method

An examinee puts the face into the face groove 24, and lays the chin on the chin rest 3, an examination system is started through a touch operation on the second display screen 23, and patient information is input; after the pressure sensing wafer 33 of the chin rest 3 senses the laying of the chin, the controller instructs the thermal camera 27 to roughly position the cheekbone position of the examinee, and the third motor sliding block 25 is started to drive the cheekbone airbag supporting column 26 to move to the cheekbone position, then an air pump is started to pump air into the hollow air plate 31, an airbag column 32 on the hollow air plate 31 is inflated to extend outwards, and the pressure sensing wafer 33 at the front end of the airbag column 32 is used for monitoring according to preset pressure; when the pressures of the pressure sensing wafers 33 at all positions are nearly the same, air pumping is stopped and kept, thus forming the fixation to the chin of the examinee, the head of the examinee extends forwards and abuts against the two cheekbone airbag supporting columns 26, the pressure sensing wafers 33 of the cheekbone air bag supporting columns 26 are used for sensing the pressure and dynamically adjusting the spacing; two airbag supporting columns 26 are used for assisting in fixation to generally position the face portion of the examinee;

then the human eye information collection assembly 4 is moved according to the human eye positioning analysis module 101, the two camera assemblies 41 are located in front of the eyes of the examinee, the transverse bracket 42b is controlled by the first motor sliding block 43 to move up and down along the longitudinal bracket 42a, and the two camera assemblies 41 are controlled by the second motor sliding block 44 to move horizontally along the transverse bracket 42b; the horizontal angles of the two camera assemblies 41 and the linear distance between the camera assemblies and the eyes of the examinee are controlled by the transmission member 5;

as shown in FIG. 2, after completing positioning, the image information collection module 103 and the imaging camera 28 are used for acquiring ophthalmic image data of the ocular surface, the ocular anterior segment and fundus of the examinee and automatically acquiring the diopter and corneal curvature simultaneously, and an AI picture quality monitoring system is used for performing quality judgment on the ocular surface image data, the ocular anterior segment image data, and the fundus image data. If the ophthalmic image data is qualified, the ophthalmic image data is taken as follow-up diagnosis data, if the ophthalmic image data is unqualified, the re-shooting is required, then the ophthalmic image data is cached in the data storage management module 107, the eye condition of the examinee is analyzed and diagnosed according to the eye disease analysis and diagnosis module 106, and generated diagnosis information and corresponding guidance and referral opinions are displayed through the second display screen 23. Simultaneously, after a report is printed, the tabletop ophthalmic robot b 2 resets to complete the diagnosis work of the examined person;

wherein, the working method of the transmission member 5 is that: the rod main body 51 is driven by the first rotating motor disc 551 to rotate, and the worm 53 is driven by the second rotating motor disc 552 to rotate, when the first rotating motor disc 551 drives the rod main body 51 to rotate, the rod main body 51 drives various toothed wheels 52 to rotate, and the toothed wheels 52 are driven to rotate through the meshing effect with the transmission type toothed ring 54, and thus the horizontal angles of the two camera assemblies 41 are adjusted by the rotating angle of the first rotating motor disc 552, the second rotating motor disc 552 drives the worm 53 to rotate, the worm 53 is in meshing transmission with the worm wheel 523 of each toothed wheel 52 to enable the worm wheel 523 to rotate, the worm wheel 523 and the spur gear 522 are in toothed belt transmission, and thus the spur gear 522 is driven to rotate; the spur gear 522 is in meshing transmission with the tooth socket 541 of the transmission type toothed ring 54, and thus the transmission type toothed ring 54 can be moved along a path formed by the adjacent assembly of the toothed wheels 52, thereby achieving adjustment of the linear distance between the two camera assemblies 41 and the eyes by the rotation of the second rotating motor disc 552.

Ophthalmic Robot and Diagnosis System Clinical Trial

Trial samples: a tabletop ophthalmic robot b 2 was selected as a trial robot, patients with three eye diseases, such as glaucoma patients, keratitis patients and cataract patients, were selected at will, 100 patients with each of the three eye diseases were selected, and 50 patients with normal eyes were selected, thereby obtaining mixed samples of 350 examinees; and the selected patient samples were free of patients with glaucoma and cataract crossover;

trail method: the 350 examinees were comprehensively judged by the tabletop ophthalmic robot b 2 with the artificial intelligence eye disease screening and diagnostic system sequentially, with a statistical result as follows:

TABLE 1

Statistical table of the number of symptom judgment for various examinees

| | Symptom | | | |
|---|---|---|---|---|
| | Glaucoma | Keratitis | Cataract | Normal |
| Number | 98 | 97 | 99 | 56 |

It can be known from the data in table 1 that the accuracy rate of screening and judging the glaucoma patients by the tabletop ophthalmic robot b 2 equipped with the artificial intelligence eye disease screening and diagnostic system is 98%, the accuracy rate of screening and judging the keratitis patients by the tabletop ophthalmic robot b 2 equipped with the artificial intelligence eye disease screening and diagnostic system is 97%. The accuracy rate of screening and judging the cataract patients by the tabletop ophthalmic robot b 2 equipped with the artificial intelligence eye disease screening and diagnostic system is 99%.

Therefore, through simple verification of the trial, the tabletop ophthalmic robot b 2 equipped with the artificial intelligence eye disease screening and diagnostic system can comprehensively diagnose the patients with the eye diseases basically, with low misdiagnosis rate; the preliminary screening of the eye diseases of the inspected people in various hospitals can be basically met, the diagnosis intensity of medical staff is reduced, and through preliminary speculation, the reasons for causing misdiagnosis are roughly divided into two types: 1) limitation of the performance of a camera element, 2) problems of information collection such as blinking of the examinee and the like (which can be used as a reference basis for improving the accuracy rate in the later period), and 3) relatively unobvious eye symptoms of the examinee.

What is claimed is:

1. An artificial intelligence eye disease screening and diagnostic system based on an ophthalmic robot, comprising:
    a human eye positioning analysis module used for controlling the ophthalmic robot to position an eye of an examinee to determine an eye position of the examinee;
    an execution control module used for executing a corresponding instruction to control the ophthalmic robot to move to the eye positions of the examinee;
    an image information collection module used for acquiring ocular surface image data, ocular anterior segment image data, and fundus image data of the eye of the examinee;
    an optometry information collection module used for synchronously acquiring diopter and corneal curvature of the eye of the examinee;
    an AI picture quality monitoring module used for performing image quality judgment on the ocular surface image data, the ocular anterior segment image data, and the fundus image data of the eye of the examinee to determine the diagnostic image data of the examinee; wherein the ocular surface image data, the ocular anterior segment image data, and the fundus image data of the eye of the examinee are taken as the diagnostic image data if the ocular surface image data, the ocular anterior segment image data, and the fundus image data of the eye of the examinee are all qualified, and if at least one of the ocular surface image data, the ocular anterior segment image data, and the fundus image data of the eye of the examinee is unqualified, the image data of the unqualified part is reacquired for quality judgement until the ocular surface image data, the ocular anterior segment image data, and the fundus image data of the eye of the examinee are all qualified;
    an eye disease analysis and diagnosis module used for analyzing eye disease symptoms according to the diagnostic image data, the diopter, and the corneal curvature of the eye of the examinee to determine the lesion types of the eye of the examinee;
    and a data storage management module used for storing a diagnosis result generated by the eye disease analysis and diagnosis module and image data collected by the image information collection module;
    wherein the artificial intelligence eye disease screening and diagnostic system is installed on a controller in a main body lower portion of the ophthalmic robot, the ophthalmic robot comprises: a combined special-shaped body consisting of a main body lower portion used for energy supply and information processing and a main body upper portion for loading components such as a human eye information collection assembly and the like up and down, and the front end face of the main body lower portion is provided with a second display screen used for observing and displaying eye information of the examinee;
    a face groove is formed at the front side face of the main body upper portion, a chin rest is arranged at the lower end in the face groove, the human eye information collection assembly is arranged at an inner wall of the face groove, and cheekbone airbag supporting columns which are connected through a third motor sliding block are further arranged at the two ends of the inner wall of the face groove; an arc-shaped cotton cushion for avoiding head blow is further arranged at an upper top face in the face groove, a thermal camera used for face thermal photographing of the face and an imaging camera used for shooting and positioning the eye are further arranged at the middle portion of the inner wall of the face groove, and LED light beads are uniformly and densely embedded on the inner wall of the face groove;
    the chin rest further comprises a hollow air plate on which dense airbag columns are equidistantly provided, and pressure sensing wafers are arranged at the front ends of the airbag columns and the front ends of the cheekbone airbag supporting columns; and
    the human eye information collection assembly comprises two symmetrically arranged camera assemblies, and a transmission rack; the transmission rack comprises a longitudinal bracket, and a transverse bracket; the transmission rack is connected to the lower bottom face of the face groove through the bottom end of the longitudinal bracket, the transverse bracket is connected to a first motor sliding block arranged on a motor sliding chute of the longitudinal bracket through the transmission member, the first motor sliding blocks at the two sides of the transmission member is each provided with a telescopic rod to be in sliding connection with the transverse bracket, and the camera assemblies are connected to second motor sliding blocks arranged on the motor sliding chutes at the two sides of the transverse bracket.

2. The system according to claim 1, wherein the method for performing eye disease screening and diagnosis using the artificial intelligence eye disease screening and diagnostic system comprises:
    S201, controlling the ophthalmic robot to position an eye of the examinee by the human eye positioning analysis module to determine the eye position of the examinee;
    S202, executing a corresponding instruction by the execution control module to control the ophthalmic robot to move to the eye positions of the examinee;
    S203, acquiring ocular surface image data, ocular anterior segment image data, and fundus image data of the eye of the examinee by the image information collection module, and synchronously acquiring diopter and corneal curvature of the eye of the examinee through the optometry information collection module;
    S204, performing image quality judgement on the ocular surface image data, the ocular anterior segment image data, and the fundus image data of the eye of the examinee by the AI picture quality monitoring module, wherein the ocular surface image data, the ocular anterior segment image data, and the fundus image data of the eye of the examinee are taken as the diagnostic image data if the ocular surface image data, the ocular anterior segment image data, and the fundus image data of the eye of the examinee are all qualified, and if at least one of the ocular surface image data, the ocular anterior segment image data, and the fundus image data of the eye of the examinee is unqualified, the image data of the unqualified part is reacquired for quality judgement until the ocular surface image data, the ocular anterior segment image data, and the fundus image data of the eye of the examinee are all qualified;

S205, analyzing eye disease symptoms by the eye disease analysis and diagnosis module according to the diagnostic image data, the diopter, and the corneal curvature of the eye of the examinee to determine the lesion types of the eye of the examinee;

and S206, storing a diagnosis result generated by the eye disease analysis and diagnosis module and image data acquired by the image information collection module by the data storage management module.

3. The system according to claim 2, wherein the step of analyzing eye disease symptoms by the eye disease analysis and diagnosis module according to the diagnostic image data, the diopter, and the corneal curvature of the eye of the examinee to determine the lesion types of the eye of the examinee comprises:

based on an eye disease diagnosis algorithm model, analyzing the eye disease symptoms according to the diagnostic image data, the diopter, and the corneal curvature of the eye of the examinee to determine the lesion types of the eye of the examinee;

a construction method of the eye disease diagnosis algorithm model comprises:

S301, acquiring a training sample set consisting of the diagnostic image data, the diopter, and the corneal curvature of multiple examinees, and diagnosis results of multiple examinees, wherein the diagnosis results of the multiple examinees are obtained by ophthalmologists performing eye disease diagnosis according to the ocular surface image data, the ocular anterior segment image data, and the fundus image data of the multiple examinees;

and S302, based on the training sample set, training a preset convolutional neural network DenseNet121 using a deep learning algorithm to obtain the eye disease diagnosis algorithm model, wherein a method for training the preset convolutional neural network DenseNet121 comprises:

step one, experimental algorithm setting:
using an SGD as an optimization algorithm, setting an initial learning rate (lr) corresponding to the algorithm as 0.001, momentum as 0.9, weight decay as 5×10-5, epoch as 80, and batch size as 64; using a learning rate decay strategy in the training process: every 20 epochs, the learning rate decays to one tenth of the original, representing as:

Lr=lr*(0.1**(epoch//20)), that is, the formula is as follows:

wherein, //takes the integer division operator, i.e., works out the integer part of the quotient (excluding the remainder), and k is the epoch;

a loss function used in experiment is a cross entropy loss:
wherein, $P_i$ and $y_i$ respectively denote the prediction probability that a classification model predicts that the image is the i-th class and the real label of the image, and n is the total number of classes of classification;

step two, experimental environment:
in the experiment, constructing a network model of the experiment using Pytorch deep learning framework, and training simultaneously on four NVIDIA TITAN RTX GPUs with video memory of 24G;

step three, data preprocessing:
scaling the picture size of the data set to 224*224 in a unified manner to meet an input requirement of the network model, and meanwhile, for enhancing generalization ability of the model, randomly rotating the picture by 90 degrees, and flipping in a horizontal direction or a vertical direction, with a random probability of 0.5; and step four, data set division:
randomly dividing the original data set into three parts: a training set, a verification set, and a testing part, accounting for 70%, 15, 15% respectively.

4. The system according to claim 3, wherein the lesion types comprise: refractive error, eyelid diseases, conjunctival diseases, corneal diseases, uveitis diseases, cataract, vitreous lesions, glaucoma, and fundus oculi diseases.

5. The system according to claim 4, wherein the artificial intelligence eye disease screening and diagnostic system is installed on the ophthalmic robot, and the ophthalmic robot is specifically a tabletop ophthalmic robot.

6. The system according to claim 3, wherein the training sample set further comprises at least one increment sample, the diagnostic image data of the at least one examinee in the at least one increment sample is obtained by performing at least one of shading adjustment, rotation, and mirror inversion on the diagnostic image data of at least one examinee of the multiple examinees.

7. The system according to claim 6, wherein the artificial intelligence eye disease screening and diagnostic system is installed on the ophthalmic robot, and the ophthalmic robot is specifically a tabletop ophthalmic robot.

8. The system according to claim 3, wherein the artificial intelligence eye disease screening and diagnostic system is installed on the ophthalmic robot, and the ophthalmic robot is specifically a tabletop ophthalmic robot.

9. The system according to claim 2, wherein performing quality judgment on the ocular surface image data, the ocular anterior segment image data, and the fundus image data of the eye of the examinee by the AI picture quality monitoring module (105) comprises: performing quality judgment on the ocular surface image data, the ocular anterior segment image data, and the fundus image data of the eye of the examinee based on an image quality judgment model, thereby determining whether the ocular surface image data, the ocular anterior segment image data, and the fundus image data of the eye of the examinee are qualified; wherein the image quality judgment model is a neural network model of DenseNet121 type.

10. The system according to claim 9, wherein the artificial intelligence eye disease screening and diagnostic system is installed on the ophthalmic robot, and the ophthalmic robot is specifically a tabletop ophthalmic robot.

11. The system according to claim 2, wherein the artificial intelligence eye disease screening and diagnostic system is installed on the ophthalmic robot, and the ophthalmic robot is specifically a tabletop ophthalmic robot.

12. The system according to claim 1, wherein the transmission member comprises a rod main body, the rod main body is equidistantly provided with multiple toothed wheels which are fixedly connected to the rod main body, and two adjacent toothed wheels are butted next to each other; each toothed wheel is hollow inside, and is circumferentially provided with three branch teeth, the far end in each branch tooth is provided with a spur gear to be in rotatable connection with the inner wall of the branch teeth, the inner near end of each branch tooth is provided with a worm wheel to be in rotating connection with the inner wall of the toothed wheel, and the worm wheel and the spur gear are in transmission through a toothed belt; the rod main body is hollow inside and is provided with a rotating worm to be in meshing transmission with each worm wheel, and a hole for abutting the worm with the worm wheel is formed in a position, corresponding to the worm wheel, of the rod main body; a transmission type toothed ring is arranged at the outer circumference of each toothed wheel in a sleeved manner, a tooth socket of the transmission type toothed ring is provided with a tooth surface in meshing transmission with the spur gear, and the transverse bracket is arranged at the outer wall of the transmission type toothed ring in a sleeved manner; a driving motor set is arranged at the rear end of the rod main body and is used for respectively driving the rod main body to rotate and driving the worm to rotate; the driving motor set comprises a first rotating motor disc, and a second rotating motor disc; the second rotating motor disc is fixed to the center of the first rotating motor disc, and is connected to the worm, and a circular area between the first rotating motor disc and the second rotating motor disc is connected to the rod main body;

an artificial intelligence eye disease screening and diagnostic system which is constructed using a deep convolutional neural network DenseNet121 training model and is used for picture quality control and eye disease screening and diagnosis is installed in the ophthalmic robot; wherein the thermal camera employs an infrared thermal induction camera, and the infrared thermal induction camera is adjusted in shape to be adaptively installed at a designated position in the face groove; the imaging camera employs a 50-million-pixel lens, and the LED light beads all employ LED light sources for shape adjustment and adaptation; and the first motor sliding block, the second motor sliding block and the third motor sliding block all employ sliding rail motors for shape adjustment and adaptation, and the driving motor set employs a rotating motor for shape modification to meet a graphic structure.

13. The system according to claim 7, wherein the examinee puts the face into the face groove, and lays the chin on the chin rest, an examination system is started through a touch operation on the second display screen, and patient information is input; after the pressure sensing wafer of the chin rest senses the laying of the chin, the controller instructs the thermal camera to roughly position the cheekbone position of the examinee, and the third motor sliding block is started to drive the cheekbone airbag supporting column to move to the cheekbone position, then an air pump is started to pump air into the hollow air plate, an airbag column on the hollow air plate is inflated to extend outwards, and the pressure sensing wafer at the front end of the airbag column is used for monitoring according to preset pressure; when the pressures of the pressure sensing wafers at all positions are nearly the same, air pumping is stopped and kept, thus forming the fixation to the chin of the examinee, the head of the examinee extends forwards and abuts against the two cheekbone airbag supporting columns, the pressure sensing wafers of the cheekbone air bag supporting columns are used for sensing the pressure and dynamically adjusting the spacing; two airbag supporting columns are used for assisting in fixation to generally position the face portion of the examinee;

then the human eye information collection assembly is moved according to the human eye positioning analysis module, the two camera assemblies are located in front of the eyes of the examinee, the transverse bracket is controlled by the first motor sliding block to move up and down along the longitudinal bracket, and the two camera assemblies are controlled by the second motor sliding block to move horizontally along the transverse bracket; the horizontal angles of the two camera assemblies and the linear distance between the camera assemblies and the eyes of the examinee are controlled by the transmission member 5;

after completing positioning, the image information collection module 103 and the imaging camera are used for acquiring ophthalmic image data of the ocular surface, the ocular anterior segment and fundus of the examinee and automatically acquiring the diopter and corneal curvature simultaneously, and an AI picture quality monitoring system is used for performing quality judgment on the ocular surface image data, the ocular anterior segment image data, and the fundus image data, If the ophthalmic image data is qualified, the ophthalmic image data is taken as follow-up diagnosis data, if the ophthalmic image data is unqualified, the re-shooting is required, then the ophthalmic image data is cached in the data storage management module 107, the eye condition of the examinee is analyzed and diagnosed according to the eye disease analysis and diagnosis module 106, and generated diagnosis information and corresponding guidance and referral opinions are displayed through the second display screen;

after a report is printed, the tabletop ophthalmic robot resets to complete the diagnosis work of the examinee;

the rod main body is driven by the first rotating motor disc to rotate, and the worm is driven by the second rotating motor disc to rotate;

when the first rotating motor disc drives the rod main body to rotate, the rod main body drives various toothed wheels to rotate, and the toothed wheels are driven to rotate through the meshing effect with the transmission type toothed ring, and thus the horizontal angles of the two camera assemblies are adjusted by the rotating angle of the first rotating motor disc; and the second rotating motor disc drives the worm to rotate, the worm is in meshing transmission with the worm wheel of each toothed wheel to enable the worm wheel to rotate, the worm wheel and the spur gear are in toothed belt transmission, and thus the spur gear is driven to rotate; the spur gear is in meshing transmission with the tooth socket of the transmission type toothed ring, and thus the transmission type toothed ring can be moved along a path formed by the adjacent assembly of the toothed wheels, thereby achieving adjustment of the linear distance between the two camera assemblies and the eyes by the rotation of the second rotating motor disc.

\* \* \* \* \*